United States Patent
Pfeiffer et al.

(10) Patent No.: US 9,360,369 B1
(45) Date of Patent: Jun. 7, 2016

(54) SYSTEM FOR DETERMINING AVERAGE ELLIPSOMETRIC PARAMETERS FOR PLANAR OR NON-PLANAR SHAPED OBJECTS, AND METHOD OF ITS USE

(71) Applicant: J.A. WOOLLAM CO., INC, Lincoln, NE (US)

(72) Inventors: Galen L. Pfeiffer, Roca, NE (US); Martin M. Liphardt, Lincoln, NE (US)

(73) Assignee: J.A. WOOLLAM CO., INC, Lincoln, NE (US)

( * ) Notice: Subject to any disclaimer, the term of this patent is extended or adjusted under 35 U.S.C. 154(b) by 0 days.

(21) Appl. No.: 14/545,786

(22) Filed: Jun. 20, 2015

Related U.S. Application Data

(60) Provisional application No. 61/998,209, filed on Jun. 23, 2014.

(51) Int. Cl.
  *G01J 4/00* (2006.01)
  *G01J 4/04* (2006.01)
(52) U.S. Cl.
  CPC ........................................ *G01J 4/04* (2013.01)

(58) Field of Classification Search
  CPC .............. G01J 4/00; G01N 21/21; G02F 1/01
  See application file for complete search history.

(56) References Cited

U.S. PATENT DOCUMENTS

| | | | | |
|---|---|---|---|---|
| 6,028,671 | A | 2/2000 | Svetkoff et al. | |
| 7,136,162 | B1 * | 11/2006 | Liphardt | G01N 21/211 356/369 |
| 7,623,237 | B1 * | 11/2009 | Liphardt | G01N 21/55 356/369 |
| 7,746,471 | B1 * | 6/2010 | Johs | G01N 21/21 356/369 |
| 7,872,751 | B2 * | 1/2011 | Liphardt | G01N 21/01 356/364 |
| 8,339,603 | B1 * | 12/2012 | Liphardt | G01N 21/211 356/369 |
| 8,467,057 | B1 * | 6/2013 | Johs | G01N 21/211 356/369 |

* cited by examiner

*Primary Examiner* — Tarifur Chowdhury
*Assistant Examiner* — Jamil Ahmed
(74) *Attorney, Agent, or Firm* — James D. Welch

(57) ABSTRACT

A system for easily determining average ellipsometric parameters based on data obtained from two different locations on a planar or non-planar shaped object, along with its method of use.

5 Claims, 3 Drawing Sheets

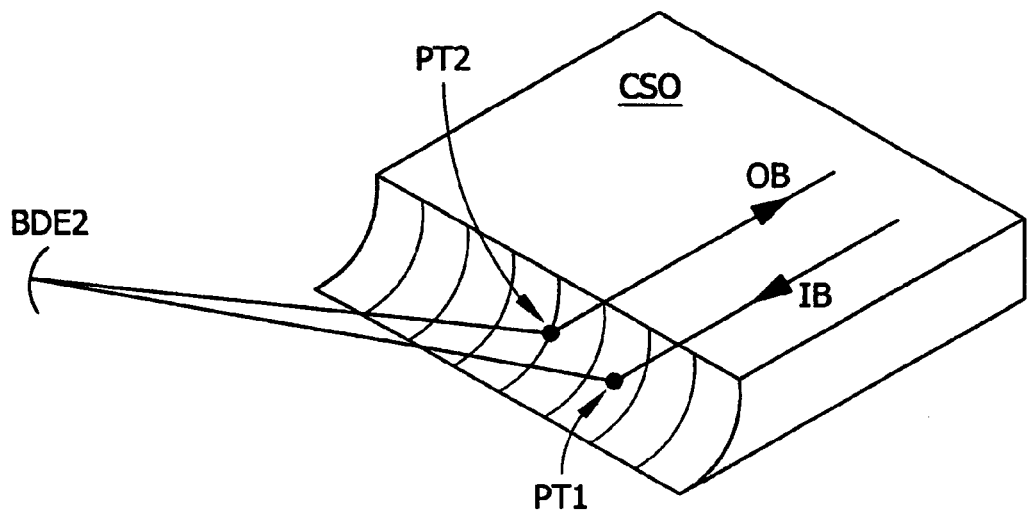
FIG. 2
FIG. 3a
FIG. 3b

SYSTEM FOR DETERMINING AVERAGE ELLIPSOMETRIC PARAMETERS FOR PLANAR OR NON-PLANAR SHAPED OBJECTS, AND METHOD OF ITS USE

This Application Claims benefit of Provisional Application No. 61/998,209 Filed Jun. 23, 2014.

TECHNICAL FIELD

The present invention is related to ellipsometer and the like systems and associated methodology, and more particularly to a system for easily determining average ellipsometric parameters based on data obtained from two different locations on a planar or non-planar shaped object, along with its method of use.

BACKGROUND

The field of Ellipsometer and the like is well known. Generally a beam of electromagnetic radiation is directed to interact with a sample and the enter a detector where a change in it's polarization state, based on said interaction with said sample, is determined. Said change is related to optical and physical properties of the sample. Typically, samples that are investigated have generally planar surfaces, but this is not always the case. At times it is of interest to, for instance, investigate items that have a non-planar shaped surface during manufacture thereof to ensure that over a sequence of such items manufacturing parameters are being properly maintained. In such cases a system that would allow a quick change of items from "off", to "on" an investigation system stage, along with quick determination of ellipsometric parameters associated therewith, would provide utility.

A number of Patents that are Assigned to the J.A. Woollam CO., Inc. provide insight to elements that such a system might include. For instance, U.S. Pat. No. 7,872,751 to Liphardt et al. describes a system for quickly setting angle of incidence (AOI), plane of incidence (POI) and Height, (of ellipsometer elements above a sample), parameters in a mapping ellipsometer or the like. U.S. Pat. No. 7,136,162 describes a system for aligning a beam to a sample surface at a known angle-of-incidence (AOI). U.S. Pat. No. 7,746,471 to Johs et al., and U.S. Pat. No. 8,339,603 to Liphardt et al. describe Flying and Mapping Ellipsometer Systems with applications to investigating the inside of a planar or non-planar tubular shaped object and to looking between two plates in a more linear system, respectively. U.S. Pat. No. 7,623,237 to Liphardt et al. and U.S. Pat. No. 8,467,057 to Johs et al. describe sample investigation and ellipsometer systems etc. that provide both a source of an electromagnetic beam, and a Detector thereof on the same side of a sample. A reflector serves to direct electromagnetic beams that impinge onto a sample back in the general direction from which they came as they approached said sample. While a Patent to Svetkoff et al., U.S. Pat. No. 6,028,671, was identified in a computer search for Patents containing the words "Concave Object" and "Ellipsometry", no Patents relevant to the present invention were identified in said computer search.

While the cited Patents arguably demonstrate elements of sample investigation systems that can be selected and modified, while rejecting other elements therewithin, there remains need for a specific system that would allow quickly and easily determining average ellipsometric parameters that correspond to data obtained from two locations on a concave object. One example of an applications for such a system would be in sequential monitoring of a series of manufactured tire rims, which, it noted, do comprise concave shapes.

DISCLOSURE OF THE INVENTION

The present invention is a system for determining average ellipsometric parameter values determined from two locations on a reflective surface of a planar or non-planar shaped object, comprising:

a) a source of, and a polarization state generator for providing a polarized incident beam of electromagnetic radiation;

b) a beam steering assembly having top and bottom elements, and wherein said top and bottom elements each have first and second openings therein, respectively;

c) a stage for supporting said planar or non-planar shaped object; and d) a polarization state detector.

In use, said source of electromagnetic radiation and polarization state generator are positioned and oriented to direct a polarized incident beam of electromagnetic radiation toward and through said first top opening in said beam steering assembly top element, such that it interacts with a first beam directing element therewithin and is directed thereby to exit from said beam steering assembly through said first bottom opening in said bottom element thereof and impinge on a first location of said reflective surface of said planar or non-planar shaped object placed on said stage for supporting it. From said first impingement location, on said reflective surface of said planar or non-planar shaped object said beam is then reflected toward and through said second bottom opening in the bottom element wherein it encounters and reflects from a second beam directing element which reflects and directs said beam back toward said planar or non-planar shaped objects so that it impinges on a second location on the reflective surface thereof, which second location is offset from the location at which the incident beam first impinged thereupon. From said second location said beam is then reflected back toward and through said first bottom opening and into said beam steering assembly wherein it encounters, and is reflected from a third beam directing element that reflects said beam through said second top opening in said top element of said beam steering assembly and into said polarization state detector as an output beam.

Said system further comprises computing system capability for determining change in polarization state set by the polarization state generator of said beam as a result of the double interaction thereof with said planar or non-planar shaped object, as detected by the polarization state detector, and providing average ellipsometric parameters therefore.

Said system can comprise focusing elements just inside said the first and possibly the second bottom openings in the bottom element of said beam steering assembly.

And, said system further comprises system capability for changing the distance between, as units:

first unit:
    said source;
    said beam steering assembly; and
    said polarization state detector; and second unit:
    said stage for supporting said planar or non-planar shaped object; and
    said planar or non-planar shaped object.

Said system capability for changing the distance between the two units just identified can be of any functional realization. It is noted that for the purposes of the present invention that only the first unit will be moved in use. The is because the planar or non-planar shaped object will generally be bulky, (eg. a tire rim), and equipment to load it onto the stage will be standardized to load each rim similarly thereto. A moving stage would therefore introduce an unnecessary complexity regarding practical use of the present invention.

In use the output beam that exits the second top opening in said top element of said beam steering assembly can be functionally directed into said polarization state detector by adjustment of said distance between said first and second units.

The present invention is also a Method of determining average ellipsometric parameters based on data obtained from two different locations (PT1) (PT2) on a planar or non-planar shaped object (CSO) comprising:

A) providing a system as described above;

B) placing a planar or non-planar shaped object on said stage (STG) for supporting said planar or non-planar shaped object (CSO);

C) causing said source (S) of electromagnetic radiation and polarization state generator (PSG) to be positioned and oriented to direct a polarized incident beam (IB) of electromagnetic radiation toward and through said first top opening (FTO) in said beam steering assembly (BSA) top element (TE) such that it interacts with a first beam directing element (BDE1) therewithin and is directed thereby to exit from said beam steering assembly (BSA) through said first bottom opening (FBO) in said bottom element (BE) thereof and impinge on a first location (PT1) of said reflective surface of said planar or non-planar shaped object (CSO) placed on said stage (STG) for supporting it, from which first impingement location (PT1) on said reflective surface of said planar or non-planar shaped object (CSO) said beam is then reflected toward and through said second bottom opening (SBO) in the bottom element (BE) wherein it encounters and reflects from a second beam directing element (BDE2) which reflects and directs said beam back toward said planar or non-planar shaped objects (CSO) so that it impinges on a second location (PT2) on the reflective surface thereof, which second location (PT2) is offset from the location (PT1) at which the incident beam (IB) first impinged thereupon, and from which second location (PT2) said beam is reflected back toward and through said first bottom opening (FBO) and into said beam steering assembly (BSA) wherein it encounters, and is reflected from a third beam directing element (BDE3) that reflects said beam through said second top opening (STO) in said top element (TE) of said beam steering assembly (BSA) and into said polarization state detector as an output beam (OB);

D) applying said computing system capability (COMP) for determining change in polarization state of said beam set by the polarization state generator (PSG) as a result of the double interaction thereof with said planar or non-planar shaped object (CSO), as detected by the polarization state detector (PSD), and providing average ellipsometric parameters therefore.

It is mentioned that FIG. 1a shows two separated Bottom openings (FBO) and (SBO), and two separate Top Openings (FTO) and (STO). This is not a critical aspect of the present invention and is to be considered demonstrative only, and not a requirement. In particular, the Top Element (TE) and Bottom Element (BE) can each be generally open, wherein the separate openings in each are essentially merged.

The present invention will be better understood by reference to the Detailed Description Section of this Specification, in conjunction with the Drawings.

BRIEF DESCRIPTION OF THE DRAWINGS

FIG. 2 shows a perspective view of a non-planar concave shaped object (CSO) with an input beam (IB) impinging on a first point thereon (PT1), and a beam reflected from a second, FIG. 1b type beam directing element (BDE2) to a second point (PT2).

FIGS. 3a and 3b show that beam directing elements (BDE1) (BDE2) can be a simple reflecting mirror, or be prism shaped.

DETAILED DESCRIPTION

Figure 1A:
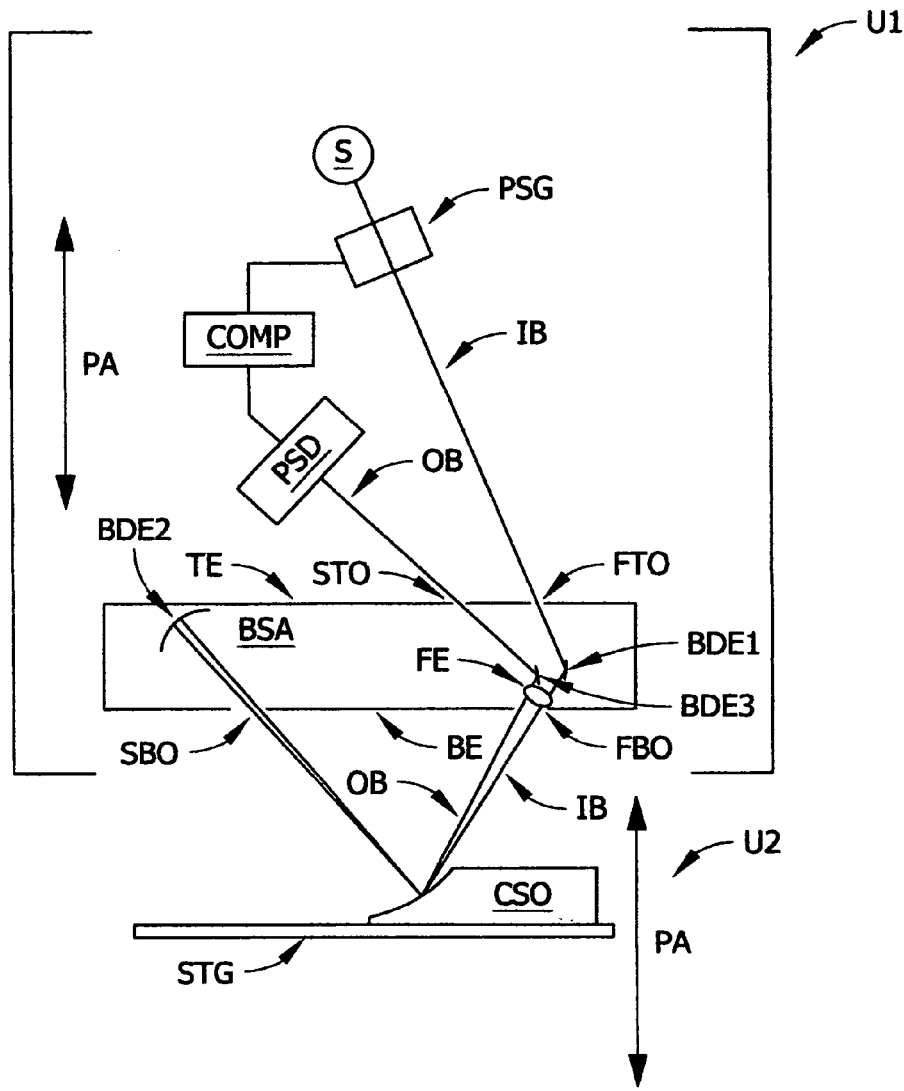
FIG. 1a shows a system for determining average ellipsometric parameter values determined from two locations (PT1) (PT2) on a demonstrative reflective surface of a non-planar concave shaped object (CSO).

Turning now to the Drawings, there is shown in FIG. 1a, a system for determining average ellipsometric parameter values determined from two locations, (PT1) (PT2), (see FIG. 2), on a reflective surface of a demonstrative non-planar concave shaped object (CSO). It is to be understood that the Drawings demonstrative presentation of a non-planar concave shaped object is not limiting, but rather is disclosing of a particularly relevant application of the present invention. The system comprises:

a) a source (S) of, and a polarization state generator (PSG) for providing a polarized incident beam (IB) of electromagnetic radiation, (note that the Source (S) can be considered to be part of the Polariation State Generator);

b) a beam steering assembly (BSA) having top (TE) and bottom (BE) elements, and wherein said top (TE) and bottom (BE) elements each have first (FTO) (FBO) and second (STO) (SBO) openings therein, respectively;

c) a stage (STG) for supporting said planar or non-planar shaped object (CSO); and d) a polarization state detector (PSD), (note a Polarization State Detector system generally comprises a Detector as well as other elements, such as an Analyzer).

Figure 1B:
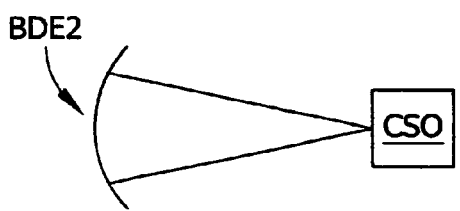
FIGS. 1b and 1c shows the reflector (BDE2) in FIG. 1a, and a functional alternative configuration in FIG. 1c.
Figure 1C:
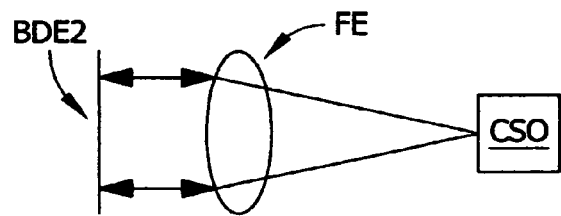
Figure 4:
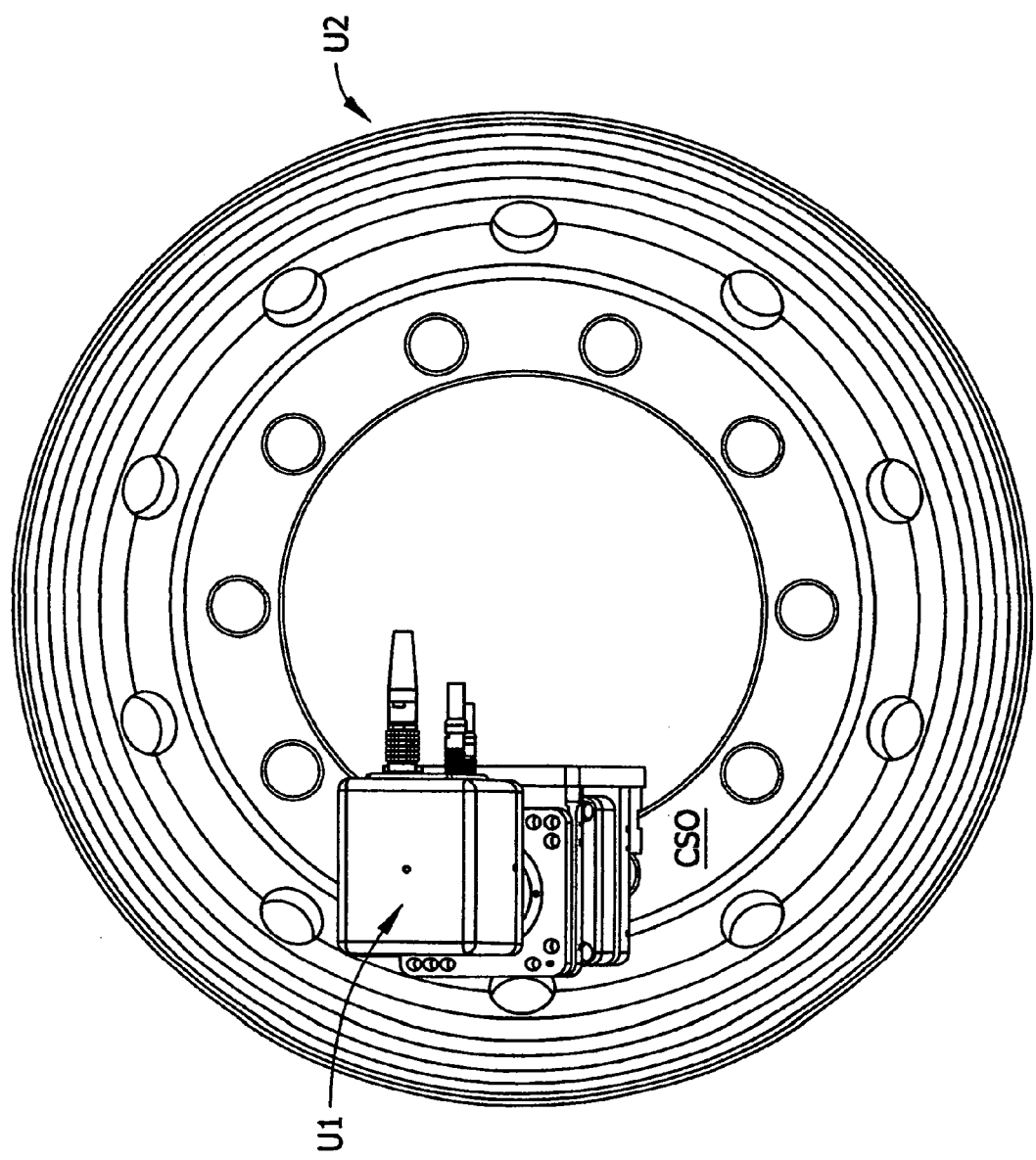
FIG. 4 shows the present invention identified as (U1), field applied in a truck tire rim, identified as (U2).

It should be noted that said source (S) of electromagnetic radiation and polarization state generator (PSG) are positioned and oriented to direct a polarized incident beam (IB) of electromagnetic radiation toward and through said first top opening (FTO) in said beam steering assembly (BSA) top element (TE) such that it interacts with a first beam directing element (BDE1) therewithin and is directed thereby to exit from said beam steering assembly (BSA) through said first bottom opening (FBO) in said bottom element (BE) thereof and impinge on a first location (PT1), (see FIG. 2), of said reflective surface of said planar or non-planar shaped object (CSO) placed on said stage (STG) for supporting it. From said first impingement location (PT1) on said reflective surface of said planar or non-planar shaped object (CSO) said beam is then reflected toward and through said second bottom opening (SBO) in the bottom element (BE) wherein it encounters and reflects from a second beam directing element (BDE2) which reflects and directs said beam back toward said planar or non-planar shaped objects (CSO) so that it impinges on a second location (PT2) on the reflective surface thereof. (Note, FIGS. 1b and 1c show alternative realizations of a functioning (BDE2) reflector). It will be observed that said second location (PT2), (see FIG. 2), is offset from the location (PT1) at which the incident beam (IB) first impinged thereupon, and from which second location (PT2) said beam is reflected back toward and through said first bottom opening (FBO) and into said beam steering assembly (BSA) wherein it encounters, and is reflected from a third beam directing element (BDE3)

that reflects said beam through said second top opening (STO) in-said top element (TE) of said beam steering assembly (BSA) and into said polarization state detector as an output beam (OB).

Said system further comprises computing system capability (COMP) for determining change in polarization state set by the polarization state generator (PSG) of said beam as a result of the double interaction thereof with said planar or non-planar shaped object (CSO), as detected by the polarization state detector (PSD), and providing average ellipsometric parameters therefore. Said Computer (COMP) capability can also be applied to control any aspect of the system in use.

Said system further comprises focusing elements (FE) just inside said the first (FBO) and second (SBO) bottom openings in the bottom element (BE) of said beam steering assembly (BSA).

Said system is also seen to further comprise system capability (PA) for changing the distance between, as units:
first unit (U1):
said source (S);
said beam steering assembly (BSA); and
said polarization state detector (PSD); and
second unit (U2):
said stage (STG) for supporting said planar or non-planar shaped object (CSO); and
said planar or non-planar shaped object.

In use the output beam (OB) that exits the second top opening (STO) in said top element (TE) of said beam steering assembly (BSA) can be functionally directed into said polarization state detector (PSD) by adjustment of said distance between said first (U1) and second (U2) units.

As a general comment, it is to be understood that the various openings in the top element (TE) and bottom element (BE), (eg. (FTO), (FBO) and (SBO) are shown as separate. However, it is to be considered that the top and bottom elements can be generally open and (FBO) and (SBO) can be merged into a generally larger opening. The only functional criteria is that a beam of electromagnetic radiation can proceed therethrough. This is to be considered within the scope of interpretation of the Claims.

It is to be understood that the major benefits of the present invention are:
It is primarily "vertically" oriented, (ie. it is "taller" than it is wide), rather than "horizontally" oriented, (ie. wider than it is tall), as is typical in most ellipsometer, polarimeter or reflectometer systems that monitor samples with electromagnetic beams that impinge on a samppe at an oblique angle of incidence. Note, the use of " " indicates that, for instance, the "vertically" terminology does not limit rotating the present invention system so that its "taller" dimension (U2), are considered. The present invention can be placed as shown with respect to such as a truck tire rim (U2), with attention being required only to height adjustment to focus the beam (IB) thereonto, because (IB) is a focused beam. Tip/Tilt of the demonstrative tire rim surface being investigated is not as relevant when a focused beam is applied thereto, as it is in most ellipsometric applications wherein a collimated bam is applied to a sample. The same is true for application of any focused beam, but the present invention takes full advantage of the effect to provide a system which is easily applicable to in-field applications. Further, note that, as best demonstrated by FIG. 2, the investigatory beam interacts twice (PT1) (PT2) with the (CSO). This provides a signal that is representative of an average value. Often such an average value is what a user of a present invention is most interested, (ie. testing during manufacturing to the check if manufacturing tolerances are being met).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for determining average ellipsometric parameter values determined from two locations (PT1) (PT2) on a reflective surface of a planar or non-planar shaped object (CSO), comprising:
    a) a source (S) of, and a polarization state generator (PSG) for providing a polarized incident beam (IB) of electromagnetic radiation;
    b) a beam steering assembly (BSA) having top (TE) and bottom (BE) elements, and wherein said top (TE) and bottom (BE) elements each have first (FTO) (FBO) and second (STO) (SBO) openings therein, respectively;
    c) a stage (STG) for supporting said planar or non-planar shaped object (CSO); and
    d) a polarization state detector (PSD);

said source (S) of electromagnetic radiation and polarization state generator (PSG) being positioned and oriented to direct a polarized incident beam (IB) of electromagnetic radiation toward and through said first top opening (FTO) in said beam steering assembly (BSA) top element (TE) such that it interacts with a first beam directing element (BDE1) therewithin and is directed thereby to exit from said beam steering assembly (BSA) through said first bottom opening (FBO) in said bottom element (BE) thereof and impinge on a first location (PT1) of said reflective surface of said planar or non-planar shaped object (CSO) placed on said stage (STG) for supporting it, from which first impingement location (PT1) on said reflective surface of said planar or non-planar shaped object (CSO) said beam is then reflected toward and through said second bottom opening (SBO) in the bottom element (BE) wherein it encounters and reflects from a second beam directing element (BDE2) which reflects and directs said beam back toward said planar or non-planar shaped objects (CSO) so that it impinges on a second location (PT2) on the reflective surface thereof, which second location (PT2) is offset from the location (PT1) at which the incident beam (IB) first impinged thereupon, and from which second location (PT2) said beam is reflected back toward and through said first bottom opening (FBO) and into said beam steering assembly (BSA) wherein it encounters, and is reflected from a third beam directing element (BDE3) that reflects said beam through said second top opening (STO) in said top element (TE) of said beam steering assembly (BSA) and into said polarization state detector as an output beam (OB);

said system further comprising computing system capability (COMP) for determining change in polarization state of said beam set by the polarization state generator (PSG) as a result of the double interaction thereof with said planar or non-planar shaped object (CSO), as detected by the polarization state detector (PSD), and providing average ellipsometric parameters therefore.

2. A system as in claim 1, which further comprises focusing elements (FE) just inside said the first (FBO) and second (SBO) bottom openings in the bottom element (BE) of said beam steering assembly (BSA).

3. A system as in claim 1, which further comprises system capability (PA) for changing the distance between, as units:
    first unit (U1):

said source (S);
said beam steering assembly (BSA); and
said polarization state detector (PSD); and
second unit (U2):
said stage (STG) for supporting said planar or non-planar shaped object (CSO); and
said planar or non-planar shaped object;
such that the output beam (OB) that exits the second top opening (STO) in said top element (TE) of said beam steering assembly (BSA) can be functionally directed into said polarization state detector (PSD) by adjustment of said distance between said first (U1) and second (U2) units.

4. A method of determining average ellipsometric parameters based on data obtained from two different locations (PT1) (PT2) on a planar or non-planar shaped object (CSO) comprising:

A) providing a system for determining average ellipsometric parameter values determined from two locations (PT1) (PT2) on a reflective surface of a planar or non-planar shaped object (CSO), comprising:
  a) a source (S) of, and a polarization state generator (PSG) for providing a polarized incident beam (IB) of electromagnetic radiation;
  b) a beam steering assembly (BSA) having top (TE) and bottom (BE) elements, and wherein said top (TE) and bottom (BE) elements each have first (FTO) (FBO) and second (STO) (SBO) openings therein, respectively;
  c) a stage (STG) for supporting said planar or non-planar shaped object (CSO); and
  d) a polarization state detector (PSD);
  said source (S) of electromagnetic radiation and polarization state generator (PSG) being positioned and oriented to direct a polarized incident beam (IB) of electromagnetic radiation toward and through said first top opening (FTO) in said beam steering assembly (BSA) top element (TE) such that it interacts with a first beam directing element (BDE1) therewithin and is directed thereby to exit from said beam steering assembly (BSA) through said first bottom opening (FBO) in said bottom element (BE) thereof and impinge on a first location (PT1) of said reflective surface of said planar or non-planar shaped object (CSO) placed on said stage (STG) for supporting it, from which first impingement location (PT1) on said reflective surface of said planar or non-planar shaped object (CSO) said beam is then reflected toward and through said second bottom opening (SBO) in the bottom element (BE) wherein it encounters and reflects from a second beam directing element (BDE2) which reflects and directs said beam back toward said planar or non-planar shaped objects (CSO) so that it impinges on a second location (PT2) on the reflective surface thereof, which second location (PT2) is offset from the location (PT1) at which the incident beam (IB) first impinged thereupon, and from which second location (PT2) said beam is reflected back toward and through said first bottom opening (FBO) and into said beam steering assembly (BSA) wherein it encounters, and is reflected from a third beam directing element (BDE3) that reflects said beam through said second top opening (STO) in said top element (TE) of said beam steering assembly (BSA) and into said polarization state detector as an output beam (OB);
  d) said system further comprising computing system capability (COMP) for determining change in polarization state of said beam set by the polarization state generator (PSG) as a result of the double interaction thereof with said planar or non-planar shaped object (CSO), as detected by the polarization state detector (PSD), and providing average ellipsometric parameters therefore;
  e) said system further comprising focusing elements (FE) just inside said the first (FBO) and second (SBO) bottom openings in the bottom element (BE) of said beam steering assembly (BSA); and
  f) said system further comprising system capability (PA) for changing the distance between, as units:
  first unit (U1):
    said source (S);
    said beam steering assembly (BSA); and
    said polarization state detector (PSD); and
  second unit (U2):
    said stage (STG) for supporting said planar or non-planar shaped object (CSO); and
    said planar or non-planar shaped object;
  such that the output beam (OB) that exits the second top opening (STO) in said top element (TE) of said beam steering assembly (BSA) can be functionally directed into said polarization state detector (PSD) by adjustment of said distance between said first (U1) and second (U2) units;

B) placing a planar or non-planar shaped object on said stage (STG) for supporting said planar or non-planar shaped object (CSO);

C) causing said source (S) of electromagnetic radiation and polarization state generator (PSG) to be positioned and oriented to direct a polarized incident beam (IB) of electromagnetic radiation toward and through said first top opening (FTO) in said beam steering assembly (BSA) top element (TE) such that it interacts with a first beam directing element (BDE1) therewithin and is directed thereby to exit from said beam steering assembly (BSA) through said first bottom opening (FBO) in said bottom element (BE) thereof and impinge on a first location (PT1) of said reflective surface of said planar or non-planar shaped object (CSO) placed on said stage (STG) for supporting it, from which first impingement location (PT1) on said reflective surface of said planar or non-planar shaped object (CSO) said beam is then reflected toward and through said second bottom opening (SBO) in the bottom element (BE) wherein it encounters and reflects from a second beam directing element (BDE2) which reflects and directs said beam back toward said planar or non-planar shaped objects (CSO) so that it impinges on a second location (PT2) on the reflective surface thereof, which second location (PT2) is offset from the location (PT1) at which the incident beam (IB) first impinged thereupon, and from which second location (PT2) said beam is reflected back toward and through said first bottom opening (FBO) and into said beam steering assembly (BSA) wherein it encounters, and is reflected from a third beam directing element (BDE3) that reflects said beam through said second top opening (STO) in said top element (TE) of said beam steering assembly (BSA) and into said polarization state detector as an output beam (OB);

D) applying said computing system capability (COMP) for determining change in polarization state of said beam set by the polarization state generator (PSG) as a result of the double interaction thereof with said planar or non-planar shaped object (CSO), as detected by the polarization state detector (PSD), and providing average ellipsometric parameters therefore.

5. A system for determining average ellipsometric parameter values determined from two locations (PT1) (PT2) on a reflective surface of a planar or non-planar shaped object (CSO), comprising:

a) a source (S)-polarization state generator (PSG) for providing a polarized incident beam (IB) of electromagnetic radiation;
b) a beam steering assembly (BSA);
c) a stage (STG) for supporting said planar or non-planar shaped object (CSO); and
d) a polarization state detector (PSD);

said source (S) of electromagnetic radiation and polarization state generator (PSG) being positioned and oriented to direct a polarized incident beam (IB) of electromagnetic radiation toward said beam steering assembly (BSA) such that it interacts with a first beam directing element (BDE1) therewithin and is directed thereby to exit from said beam steering assembly (BSA) impinge on a first location (PT1) of said reflective surface of said planar or non-planar shaped object (CSO) placed on said stage (STG) for supporting it, from which first impingement location (PT1) on said reflective surface of said planar or non-planar shaped object (CSO) said beam encounters and reflects from a second beam directing element (BDE2) which reflects and directs said beam back toward said planar or non-planar shaped objects (CSO) so that it impinges on a second location (PT2) on the reflective surface thereof, which second location (PT2) is offset from the location (PT1) at which the incident beam (IB) first impinged thereupon, and from which second location (PT2) said beam is reflected into said beam steering assembly (BSA) wherein it encounters, and is reflected from a third beam directing element (BDE3) that reflects said beam into said polarization state detector as an output beam (OB);

said system further comprising computing system capability (COMP) for determining change in polarization state of said beam set by the polarization state generator (PSG) as a result of the double interaction thereof with said planar or non-planar shaped object (CSO), as detected by the polarization state detector (PSD), and providing average ellipsometric parameters therefore.

\* \* \* \* \*